(12) United States Patent
Oue et al.

(10) Patent No.: US 8,974,750 B2
(45) Date of Patent: Mar. 10, 2015

(54) NOZZLE DEVICE AND LIQUID SAMPLE ANALYZER

(75) Inventors: Soichi Oue, Kyoto (JP); Yoshihiro Yano, Kyoto (JP); Narihiro Oku, Kyoto (JP)

(73) Assignee: Horiba, Ltd., Kyoto (JP)

( * ) Notice: Subject to any disclaimer, the term of this patent is extended or adjusted under 35 U.S.C. 154(b) by 667 days.

(21) Appl. No.: 12/810,805

(22) PCT Filed: Dec. 18, 2008

(86) PCT No.: PCT/JP2008/073071
§ 371 (c)(1),
(2), (4) Date: Jun. 25, 2010

(87) PCT Pub. No.: WO2009/084451
PCT Pub. Date: Jul. 9, 2009

(65) Prior Publication Data
US 2010/0273243 A1    Oct. 28, 2010

(30) Foreign Application Priority Data

Dec. 27, 2007  (JP) ................ 2007-336286
Dec. 27, 2007  (JP) ................ 2007-337965

(51) Int. Cl.
*G01N 1/02*  (2006.01)
*G01N 1/10*  (2006.01)
(Continued)

(52) U.S. Cl.
CPC ........ *G01N 35/1016* (2013.01); *G01N 35/1079* (2013.01); *G01N 2035/1023* (2013.01)
USPC ..... 422/512; 422/509; 73/863.01; 73/863.81; 73/863.85; 73/863.86

(58) Field of Classification Search
USPC ................ 422/509, 512; 73/863.01, 73/863.81–863.86
See application file for complete search history.

(56) References Cited

U.S. PATENT DOCUMENTS 4,887,472 A * 12/1989 Jansen ............... 73/863.86
5,935,523 A *  8/1999 McCandless et al. ...... 422/510
6,324,926 B1 * 12/2001 Lehtinen et al. .......... 73/864.24
(Continued)

FOREIGN PATENT DOCUMENTS

CN      1928526      3/2007
EP    0 220 430      5/1987
(Continued)

OTHER PUBLICATIONS http://dictionary.reference.com/browse/tap?s=t.*
(Continued)

*Primary Examiner* — Jan Ludlow (57) ABSTRACT

A nozzle device which can perform accurate quantitative suction without being affected by a pressure when, for example, a nozzle (2) is inserted into a closed container (T). The nozzle device has the nozzle (2) that is inserted into the closed container
(T) and that sucks a liquid in the closed container (T), an exposure to atmosphere mechanism (3) that opens the closed container (T) to the atmospheric air, and an opening/closing structure (4) that is arranged at a proximal end of the nozzle (2) and that has an internal flow channel (411) communicated with a flow channel in the nozzle (2) and an opening/closing mechanism for opening and closing the internal flow channel (411), and an opening/closing control section (5) that controls the opening/closing mechanism.

9 Claims, 7 Drawing Sheets

(51) Int. Cl.
  *G01N 1/22* (2006.01)
  *G01N 35/10* (2006.01)

(56) References Cited

U.S. PATENT DOCUMENTS

| | | | |
|---|---|---|---|
| 2005/0118061 | A1 | 6/2005 | Mototsu |
| 2007/0062316 | A1 | 3/2007 | Kitagawa et al. |
| 2008/0060413 | A1 | 3/2008 | Miyamoto et al. |

FOREIGN PATENT DOCUMENTS

| | | |
|---|---|---|
| JE | 11-118810 | 4/1999 |
| JO | 1991-048767 | 5/1991 |
| JP | 59-097058 | 6/1984 |
| JP | 62-110158 | 5/1987 |
| JP | 63-92253 | 6/1988 |
| JP | 63-159764 | 7/1988 |
| JP | 01-191033 | 8/1989 |
| JP | 4-500732 | 2/1992 |
| JP | 04-252960 | 9/1992 |
| JP | 05-264561 | 10/1993 |
| JP | 6-28737 | 4/1994 |
| JP | 06-253812 | 9/1994 |
| JP | 07-072143 | 3/1995 |
| JP | 07-083938 | 3/1995 |
| JP | 11-038017 | 2/1999 |
| JP | 11-295317 | 10/1999 |
| JP | 11-295321 | 10/1999 |
| JP | 2002-055110 | 2/2002 |
| JP | 2002-228670 | 8/2002 |
| JP | 2003-302411 | 10/2003 |
| JP | 2003-315350 | 11/2003 |
| JP | 2004-003916 | 1/2004 |
| JP | 2004-170156 | 6/2004 |
| JP | 2005-233765 | 9/2005 |
| JP | 2006-292732 | 10/2006 |
| JP | 2008-542689 | 11/2008 |
| WO | 91/01007 | 1/1991 |
| WO | 2006/121789 | 11/2006 |
| WO | 2007/023889 | 3/2007 |

OTHER PUBLICATIONS

Japanese Application No. 2007-336286 Office Action dated Jan. 31, 2012, 3 pages.
Japanese Application No. 2007-336286 Office Action dated May 24, 2011, 3 pages.
Chinese Application No. 200880117967.0 Office Action dated Aug. 3, 2012, 6 pages.
Japanese Application No. 2007-337965 Office Action dated May 24, 2011, 3 pages.

* cited by examiner

NOZZLE DEVICE AND LIQUID SAMPLE ANALYZER

The present application claims priority from PCT/JP2008/073071 filed on Dec. 18, 2008 which claims priority from Japanese Patent Application 2007-337965 filed Dec. 27, 2007 and Japanese Patent Application 2007-336286 filed on Dec. 27, 2007.

FIELD OF THE ART

This invention relates to a nozzle device for sucking a liquid from a closed container and a liquid sample analyzer using the nozzle device.

BACKGROUND ART

Conventionally, a liquid sample analyzer, especially, a device for analyzing a biological sample such as blood comprises a nozzle that is inserted into a sample container as a closed container and a suction mechanism such as a syringe to suck a liquid sample such as blood from the nozzle. The nozzle and the suction mechanism are connected by an elastic tube having elasticity.

However, in case that a pressure in the sample container is bigger than a pressure (atmospheric pressure) in the elastic tube, when the nozzle is inserted into the sample container, there is no space left for the pressure in the sample container and the pressure in the nozzle to escape because the sample container and the elastic tube are in a tightly closed state. As a result, the pressure in the elastic tube rises and becomes in a pressurized state during a process while the pressure in the sample container and the pressure in the elastic tube change to an equilibrium state. At this time, the elastic tube fails to keep its volume constant against the pressure and inflates. Then the blood enters the nozzle by an amount that the elastic tube inflates. Once the blood enters the nozzle, a slight amount of the blood attaches an inner wall of the nozzle and remains in the nozzle, even though the pressure in the sample container later becomes the atmospheric pressure.

In addition, in case that the flow channel in the nozzle, the elastic tube and the syringe are filled with a liquid such as a diluted solution, when the blood enters the nozzle, the blood is mixed with the liquid so that the blood still remains in the nozzle.

As mentioned, in case that the quantitative determination is conducted based on a volume of a flow channel in the nozzle and a volume of a flow channel in the elastic tube, there is a problem that it fails to conduct an accurate quantitative determination. Meanwhile, in case that the pressure in the sample container is smaller than the atmospheric pressure, an adverse phenomenon occurs. Then in case that the nozzle is filled with a liquid such as a diluted solution, the liquid flows into the closed container from the nozzle and the blood is diluted by the liquid, resulting in failing the accurate quantitative determination.

In order to solve these problems, as shown in the patent document 1, there is an arrangement wherein a means to open the closed container to the atmosphere is arranged in the nozzle.

However, with this arrangement, it fails to deal with a rapid pressure change at a moment when the nozzle is inserted into the closed container or at a time when the nozzle is pulled out from the closed container so that there is still the above-mentioned problem. Patent document 1: Japan patent laid-open number 2004-170156

DISCLOSURE OF THE INVENTION

Problems to be Solved by the Invention

The present claimed invention intends to solve all of the problems and a main object of this invention is to enable an accurate quantitative suction without being affected by a pressure generated at a time when a nozzle is inserted into a closed container.

Means to Solve the Problems

More specifically, a nozzle device in accordance with this invention is characterized by comprising a nozzle that is inserted into a closed container and that sucks a liquid in the closed container, an exposure to atmosphere mechanism that opens the closed container to the atmospheric air, an opening/closing structure that is connected to a proximal end part of the nozzle and that has an internal flow channel communicated with a flow channel in the nozzle and an opening/closing mechanism for opening and closing the internal flow channel, and an opening/closing control section that controls the opening/closing mechanism.

In accordance with this arrangement, since the elastic tube will not transform because of no pressure influence on the elastic tube when the nozzle is inserted into the closed container, it is possible to eliminate a suction error caused by a volume change in the elastic tube. As a result, an accurate quantitative suction can be performed.

In order to simplify a structure of the opening/closing structure, it is preferable that the opening/closing structure comprises a manifold having the internal flow channel communicated with the flow channel in the nozzle and a solenoid valve arranged in the manifold.

As a concrete embodiment of the opening/closing structure, it is preferable that the internal flow channel of the opening/closing structure is not transformed by a differential pressure between the atmospheric pressure and a pressure in the closed container.

In order to eliminate the difference between the atmospheric pressure and the pressure in the closed container by exposing the closed container to the atmospheric air by means of the exposure to atmosphere mechanism and to avoid a pressure influence during a process of exposing the closed container to the atmospheric air, it is preferable that the opening/closing control section controls the opening/closing mechanism so as to block up the internal flow channel both at a time when the nozzle is inserted into the closed container and until a predetermined period after the nozzle is inserted into the closed container.

In order to avoid an influence from a pressure change generated at a time of pulling the nozzle out of the closed container, it is preferable that the opening/closing control section controls the opening/closing mechanism so as to block up the internal flow channel at a time when the nozzle is pulled out of the closed container.

In addition, the liquid sample analyzer in accordance with this invention has the above-mentioned nozzle device, a suction mechanism that is connected to the opening/closing structure and that is to suck the liquid in the closed container through the nozzle, and a suction control section that controls the suction mechanism.

With this arrangement, in order to enable an accurate quantitative suction by conducting suction after the closed container is exposed to the atmospheric air, it is preferable that the suction control section sucks the liquid from the closed container at a time when a predetermined period passes after the nozzle is inserted into the closed container.

EFFECT OF THE INVENTION

In accordance with this invention, it is possible to enable an accurate quantitative suction without being affected by the pressure at a time when the nozzle is inserted into the closed container.

EXPLANATION OF THE CODES

1 . . . liquid sample sucking device
T . . . closed container
2 . . . nozzle
3 . . . exposure to atmosphere mechanism
4 . . . opening/closing structure
411, 412 . . . internal flow channel
41 . . . manifold
42 . . . opening/closing mechanism (solenoid valve)
5 . . . opening/closing control section
6 . . . suction mechanism
7 . . . suction control section
8 . . . CPU
Z1 . . . specimen sampling device
Z2 . . . angle setting mechanism (elastic member, compression coil spring)
Z3 . . . sample container
Z5 . . . sampling nozzle
Z8 . . . position adjusting mechanism Best Modes Of Embodying The Invention <First Embodiment>

Figure 1:
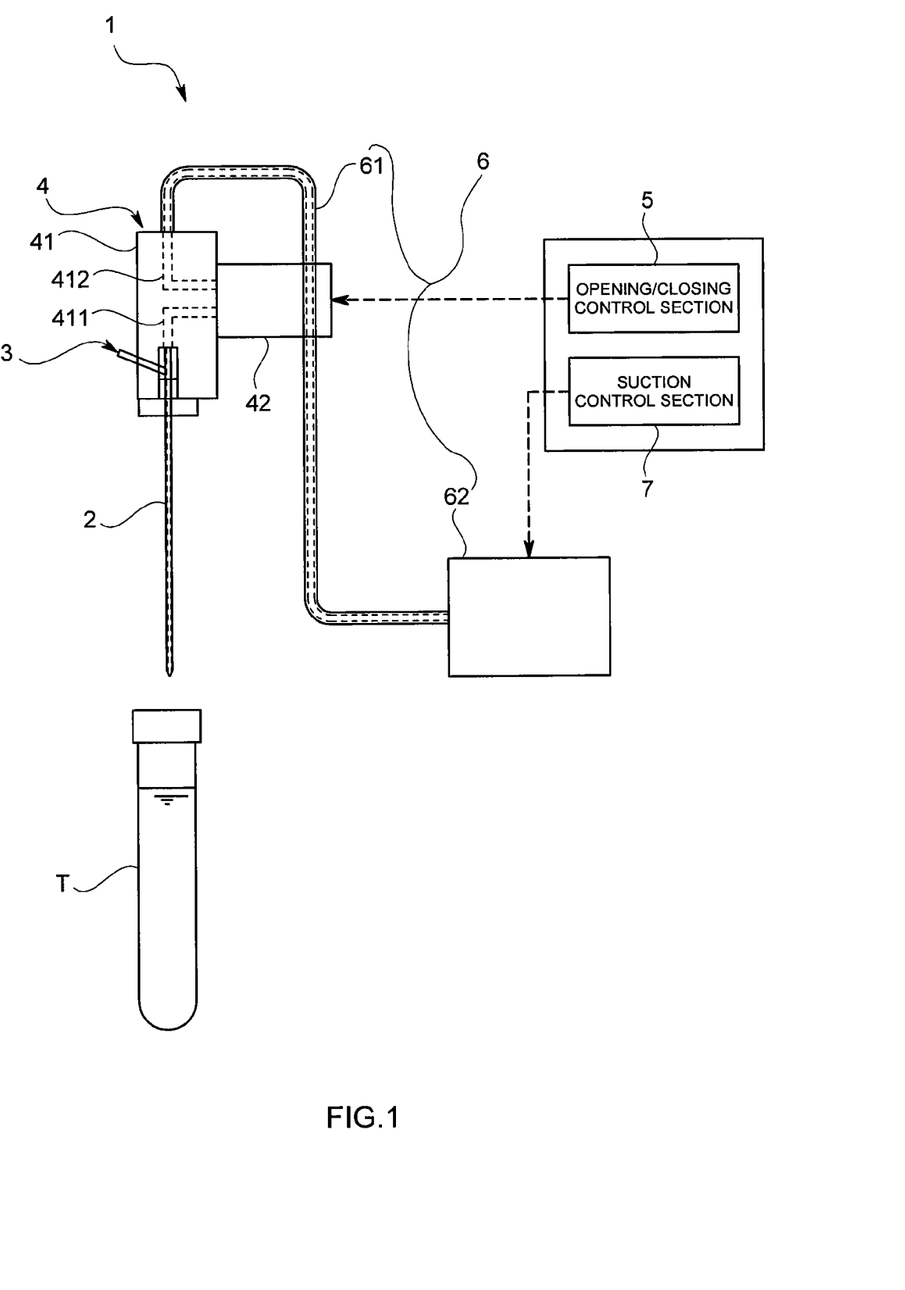
FIG. 1 is a pattern configuration diagram of a liquid sample sucking device in accordance with one embodiment of this invention.

Next, a first embodiment of a liquid sample sucking device (a specimen sampling device) 1 using a nozzle device in accordance with this invention will be explained with reference to drawings. FIG. 1 is a pattern structure views of the liquid sample sucking device 1 in accordance with this embodiment.

<Configuration>

The liquid sample sucking device 1 in accordance with this embodiment is used for a liquid sample analyzer, for example, a blood analyzer, to analyze a biological sample, and conducts quantitative suction (conducts sampling) of the blood (sample) in a closed container T without being affected by a pressure in the closed container T.

The blood analyzer measures WBC (a number of a white blood cell), RBC (a number of a red blood cell), PLT (a number of a platelet), MCV (a volume of a red cell volume) and Hct (a hematocrit value) by an electric resistance method and measures Hgb (a hemoglobin concentration) by an absorptiometric method in a cyanmethemoglobin method (HiCN).

More concretely, the liquid sample sucking device 1 comprises, as shown in FIG. 1, a nozzle 2 that is inserted into a closed or sealed container T and that sucks the liquid in the closed container T, an exposure to atmosphere mechanism 3 that is arranged in the nozzle 2 and that exposes the closed container T to the atmosphere at a time when the nozzle 2 is inserted into the closed container T. An opening/closing structure 4 that is arranged at a proximal end part of the nozzle 2 and that has first and second internal flow channels 411, 412 communicated with a flow channel in the nozzle 2 and an opening/closing mechanism to open/close the internal flow channels 411, 412. An opening/closing control section 5 that controls the opening/closing mechanism, a suction mechanism 6 that is connected to the opening/closing structure 4 and that has an elastic tube 61 and a syringe 62 to suck the liquid from the closed container T, and a suction control section 7 that controls the suction mechanism 6. The closed container T in this embodiment is made of a resin in a cylindrical shape with its upper opening closed by a cover (a cap) made of, for example, a resin.

Next, each component 2~7 will be explained.

Figure 3:
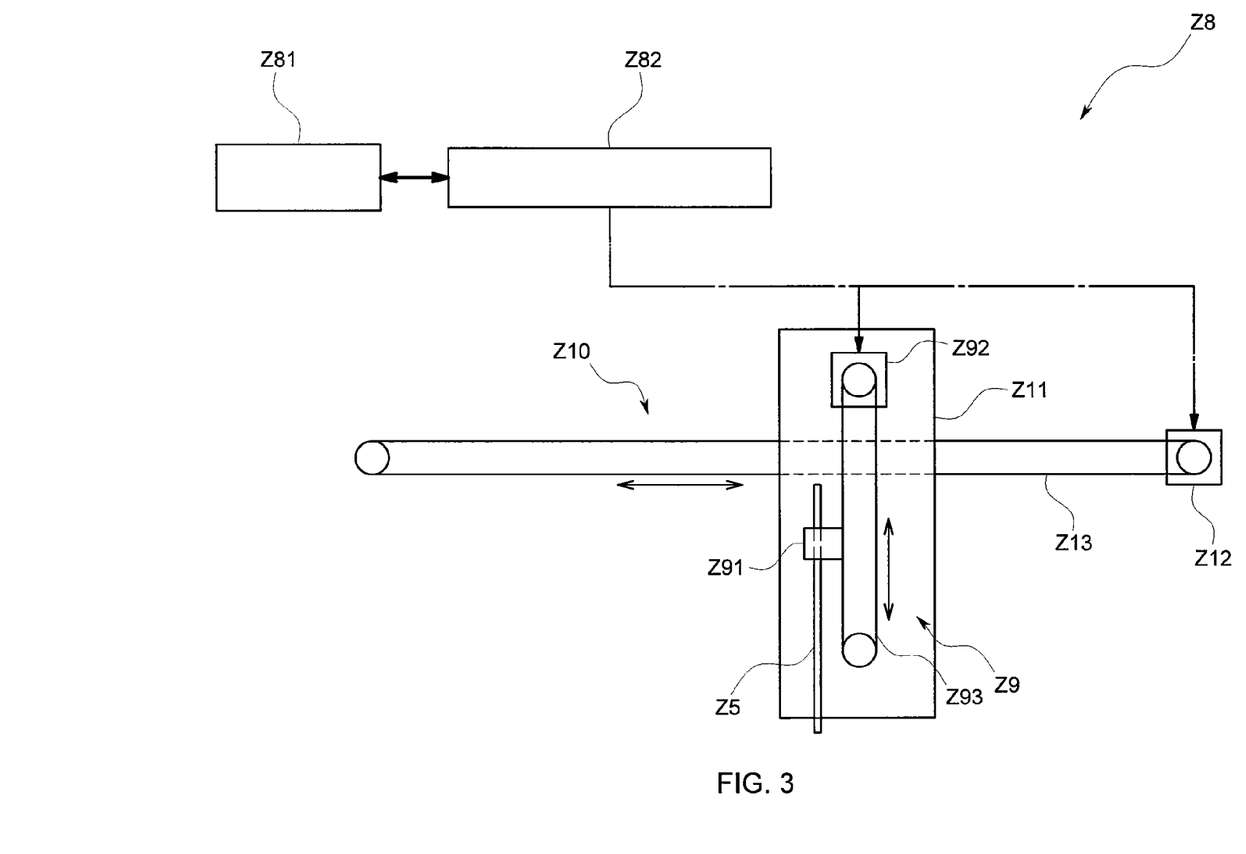
FIG. 3 is a pattern configuration diagram of a position adjusting mechanism in accordance with this embodiment.

The nozzle 2 is moved horizontally and vertically by a nozzle driving mechanism, not shown in FIG. 1, but shown in FIG. 3, so as to be inserted into the sample container as being the closed container T. The nozzle 2 in this embodiment is a double-channel structure comprising an inner tube having a liquid influent opening at a distal end part thereof and a liquid discharge opening at a proximal end part thereof and an outer tube arranged outside of the inner tube with leaving a predetermined space and having an opening at a distal end part and a proximal end part respectively. Just like the internal flow channel 411, 412, the elastic tube 61 and the syringe 62, the inner tube of the nozzle 2 is filled with a liquid such as a diluted solution.

The exposure to atmosphere mechanism 3 that exposes the sample container T to the atmosphere at a time when the nozzle 2 is inserted into the sample container T is formed by the openings arranged at both the distal end part and the proximal end part of the outer tube and a space between the inner tube and the outer tube.

The opening/closing structure 4 is arranged between the nozzle 2 and the elastic tube 61, and comprises a manifold 41 having the internal flow channels 411, 412 communicated with the flow channel in the nozzle 2 and an electromagnetic valve 42 arranged in the manifold 41.

The manifold 41 comprises the first internal flow channel 411 that is communicated with the flow channel in the nozzle 2 and that opens at a side surface of the manifold 41 and the second internal flow channel 412 that opens at the side surface of the manifold 41 and that opens at a connection port to which the elastic tube 61 is connected. And the electromagnetic valve 42 is arranged at the side surface where the first internal flow channel 411 and the second internal flow channel 412 open.

Concretely, the manifold 41 is made of a rigid material so that the internal flow channels 411, 412 are not transformed by a differential pressure between the atmospheric pressure and the pressure in the closed container T. More specifically, the manifold 41 is so made that a volume of the internal flow channel 411 and a volume of the internal flow channel 412 are kept substantially constant within a range where the differential pressure between the pressure in the sample container T tightly closed by the cover made of a resin, namely, the pressure in the closed container T and the atmospheric pressure is ±100 kPa. Namely, the manifold 41 is not transformed by the above-mentioned differential pressure. As the material of the manifold 41 conceived is, for example, a metal such as aluminum or stainless steel, or plastic such as a polyphenyl-sulphite (PPS) resin or an acrylic resin.

The opening/closing control section 5 opens or closes the internal flow channels 411, 412 by controlling the electromagnetic valve 42.

Concretely, the opening/closing control section 5 closes the internal flow channel 411 by means of the electromagnetic valve 42 at a time when the nozzle 2 is inserted into the closed container T and until a predetermined period after the nozzle 2 is inserted into the closed container T, namely, until the pressure in the closed container T is stabilized after the nozzle 2 is inserted into the closed container T and the closed container T is exposed to atmospheric pressure by means of the exposure to atmosphere mechanism 3. With this arrangement, it is possible to prevent the blood from flowing into the nozzle 2 or to prevent the diluted solution from flowing out from the nozzle 2 during the process of exposing the closed container T to the atmosphere.

Furthermore, the opening/closing control section 5 closes the internal flow channel 411 by means of the electromagnetic valve 42 at a time when the nozzle 2 is taken out from the closed container T. With this arrangement, it is possible to prevent the sucked blood from flowing out from the nozzle 2 due to the pressure change in the closed container T generated at a time when the nozzle 2 is taken out.

The suction mechanism 6 comprises the elastic tube 61 that has flexibility and whose one end is connected to the manifold 41, and the suction means 62 such as the syringe that is connected to the other end of the elastic tube 61. The suction means 62 is controlled by the suction control section 7.

The suction control section 7 conducts a quantitative determination of the blood sucked by the nozzle 2 by controlling the suction means 62. For example, the suction control section 7 conducts time control by controlling the driving time of the syringe 62 or stroke quantity control by controlling a stroke quantity of the syringe 62. More concretely, the suction control section 7 controls the suction means 62 after a predetermined time passes after the nozzle 2 is inserted into the closed container T, namely after the pressure in the closed container T is stabilized by the atmospheric pressure after the nozzle 2 is inserted into the closed container T.

The opening/closing control section 5 and the suction control section 7, shown in FIG. 1, are configured by operating a CPU 8 of an information processing unit and its peripheral devices based on programs stored in a predetermined area of an internal memory of the information processing unit.

<Operation of this Embodiment>

Next, a sucking operation of the liquid sample sucking device 1 having the above arrangement will be explained.

First, the opening/closing control section 5 closes the internal flow channel 411 in the manifold 41 by operating the electromagnetic valve 42. Then a nozzle driving section drives the nozzle 2 to be inserted into the closed container T and to lower a distal end part of the nozzle 2 to reach under a liquid level. At this time the pressure in the closed container T becomes the atmospheric pressure by the exposure to atmosphere mechanism 3 arranged in the nozzle 2. After passing the predetermined time, the opening/closing control section 5 opens the internal flow channel 411 by operating the electromagnetic valve 42.

Next, the suction control section 7 sucks the liquid by operating the syringe (the suction means 62). After sucking a predetermined quantity of the liquid, the opening/closing control section 5 closes the internal flow channel 411 by operating the electromagnetic valve 42. Later, the nozzle 2 is pulled out from the closed container T by means of the nozzle driving section. As mentioned, it is possible to suck a certain amount of the blood without generating a problem due to an imbalance between the atmospheric pressure and the pressure in the closed container T.

<Effect of this Embodiment>

In accordance with the liquid sample sucking device 1 of this embodiment having the above arrangement, since the opening/closing structure 4 is arranged between the elastic tube 61 and the nozzle 2 and the elastic tube 61 will not transform because of a pressure influence when the nozzle 2 is inserted into the closed container T, it is possible to eliminate a suction error caused by a volume change in the elastic tube 61. As a result, an accurate quantitative suction can be performed.

The present claimed invention is not limited to the first embodiment.

For example, concerning the exposure to atmosphere mechanism, in addition to the structure of the double tube, the structure of the exposure to atmosphere mechanism may be so that the nozzle comprises a tube for suction and a tube for exposure to the atmosphere each of which is arranged in parallel, or the structure may be a groove that is arranged on an outer circumferential surface of the nozzle and that communicates a space in the closed container T and an outside space at a time when the nozzle 2 is inserted into the closed container T. In addition, the exposure to atmosphere mechanism is not limited to arranging in the nozzle and may be arranged separately from the nozzle.

Concerning the opening/closing mechanism, in addition to the arrangement of using the electromagnetic valve in the above-mentioned embodiment, it may use an opening/closing valve other than the electromagnetic valve.

The opening/closing structure in the above-mentioned embodiment comprises the manifold and the electromagnetic valve, however, it may comprise a tubular member whose one end is connected to the nozzle and whose other end is connected to the elastic tube, and the opening/closing mechanism such as the electromagnetic valve that is arranged in the tubular member to open and close an internal flow channel of the tubular member. The tubular member is not transformed by a differential pressure between the atmospheric pressure and the pressure in the closed container T, and is made of a material that is the same as that of the manifold in the above-mentioned embodiment.

In addition, the liquid sample sucking device of the above-mentioned embodiment can be used for a device for processing a liquid sample such as a biological sample contained in a closed container, in addition to the blood analyzer.

<Second Embodiment>

Next, a liquid sample sucking device (a liquid sampling device) in accordance with a second embodiment will be explained. In this embodiment, components will be explained by the use of codes different from those of the first embodiment.

The invention of the second embodiment relates to a specimen sampling device that can conduct sampling of the liquid sample even though the liquid sample is in minute amounts.

Some sampling device that conducts sampling of a liquid sample contained in a sample container by the use of a sampling nozzle has an arrangement wherein a tapered and sharp distal end of the sampling nozzle is inserted into a cover of the sample container so as to reach a sample liquid in the sample container in a state that the cover of the sample container is closed.

Figure 7:
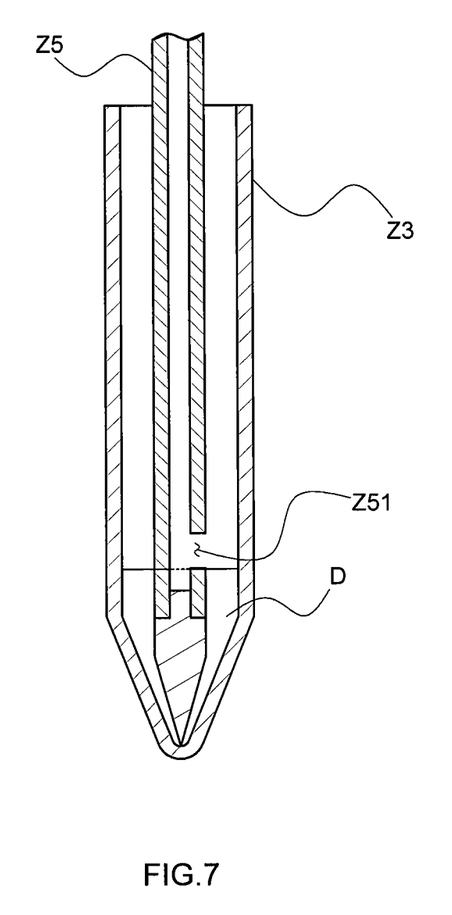
FIG. 7 is a view showing a dead space formed at a time when a sampling nozzle whose distal end is tapered is inserted into a sample container.

However, as shown in FIG. 7, since the sampling nozzle Z5 whose distal end is tapered is provided with a sampling orifice Z51 on a side circumferential surface thereof, a dead space D is formed on a bottom in the sample container Z3 and there will be a problem of failing sampling of an amount of the liquid sample corresponding to the dead space D. This problem becomes especially serious in case that the amount of the sample is very small.

As countermeasures for avoiding this problem represented are:
(1) A needle for opening the cover of the sample container is separately prepared and the cover of the sample container is bored by the use of the needle in advance, and then a sampling nozzle that has a uniform thickness and at a distal end of which a sampling orifice is formed is passed through the hole formed on the cover and the sample is sucked through the nozzle.
(2) Two sampling mechanisms are prepared so as to cope with two cases; in case that an amount of the sample is small, the sample is contained in a sample container without a cover and sampling is conducted by the use of a nozzle that has a uniform thickness and at a distal end of which a sampling orifice is formed, and in case that an amount of the sample is sufficient, the sample is contained in a sample container having a cover and sampling is conducted by the use of a nozzle whose distal end is sharp. This arrangement makes the sampling device complicated.

The patent document 2 (Japan patent laid-open number 11-295317) discloses a device for extracting a reagent that can suck all of an expensive reagent completely by the use of a sampling nozzle in a state a reagent container is tilted. However, with the device described in the patent document 2, since a tilt angle of a surface on which the reagent container is placed is fixed, it is not possible to cope with various shapes of a bottom of the reagent container. In addition, with the device described in the patent document 2, since a dead space is formed in case of using a sampling nozzle whose distal end is tapered, it is not possible to conduct sampling of all amount of the reagent.

Then this invention intends to provide a specimen sampling device that can conduct a sampling of a small amount of the liquid sample preferably in spite of using a sampling nozzle whose distal end is tapered.

More specifically, the specimen sampling device in accordance with this invention is characterized by comprising an angle setting mechanism that supports a sample container so that a tilt angle of the sample container can be changed, a position adjusting mechanism that supports the sample container and/or a sampling nozzle so that the sampling nozzle can be moved relative to the sample container, and the sampling nozzle on a lateral surface of which a sampling orifice opens.

In accordance with this arrangement, since it is possible to adjust a position to insert the sampling nozzle in accordance with the tilt angle of the sample container supported by the angle setting mechanism so as to enable insertion of the sampling nozzle along an inner side surface of the sample container, it is possible to suck the liquid sample preferably from the sampling orifice formed on the lateral surface of the sampling nozzle even though the liquid sample is in a small amount.

More concretely, for example, in case of using the sample container whose bottom inner surface is tapered and the sampling nozzle whose distal end is tapered, if the sampling nozzle is gradually inserted into the sample container along the inner side surface of the sample container, the sample container is gradually tilted to a direction opposite to the sampling nozzle so that a void is formed between the inner surface of the sample container and the sampling nozzle. And the liquid sample contained in the sample container moves upwards in the void formed because of a capillary phenomenon and then reaches a position of the sampling orifice arranged on the lateral surface of the sampling nozzle. As a result, it is possible to suck the liquid sample even though the liquid sample is in a small amount.

The angle setting mechanism is a mechanism to tilt the sample container at a predetermined angle, and represented by, for example, an elastic member. The elastic member is not limited to a specific one, and may be a compression coil spring, an elastic material made of a synthetic resin and rubber.

The specimen inspection device comprising the specimen sampling device in accordance with this invention is also one of this invention.

As mentioned, in accordance with this invention, it is possible to suck the liquid sample preferably even though the liquid sample is in a small amount.

Figure 2:
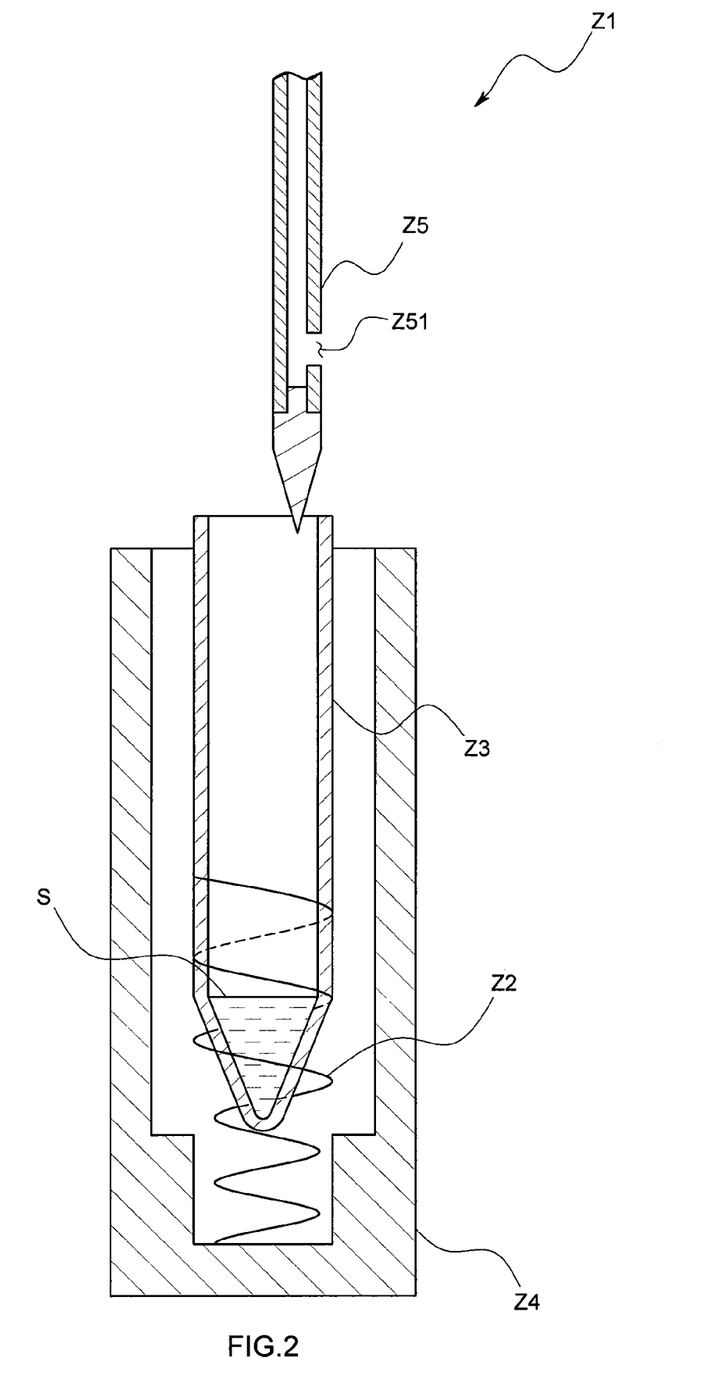
FIG. 2 is a pattern cross-sectional view of the specimen sampling device in accordance with one embodiment of this invention.

The specimen sampling device Z1 in accordance with the second embodiment comprises, as shown in FIG. 2 and FIG. 3, an elastic member as being an angle setting mechanism Z2 that supports a sample container Z3 so that a tilt angle of the sample container Z3 can be changed, a position adjusting mechanism Z8 that supports the sampling nozzle Z5 so that the sampling nozzle Z5 can move, and the sampling nozzle Z5 on a side circumferential surface of which a sampling orifice opens.

The elastic member Z2 is, concretely, a compression coil spring, and is arranged on a bottom of a sample container case Z4. The sample container case Z4 comprises an internal space so that a sufficient space remains around the sample container Z3 in a state that the sample container case Z4 contains the sample container Z3.

The position adjusting mechanism Z8 comprises, as shown in FIG. 3, a vertical direction driving mechanism Z9 and a horizontal direction driving mechanism Z10.

The vertical direction driving mechanism Z9 moves a nozzle holding member Z91 that holds the sampling nozzle Z5 in a vertical direction by means of a timing belt Z93 driven by a motor Z92.

The horizontal direction driving mechanism Z10 moves a nozzle unit Z11 comprising the vertical direction driving mechanism Z9 in a horizontal direction by means of a timing belt Z13 driven by a motor Z12.

These driving mechanisms Z9, Z10 move the sampling nozzle Z5 both in the vertical direction and in the horizontal direction so as to enable selection of the position where the sampling nozzle Z5 is inserted into the sample container Z3 by the motors Z92, Z12 driven by a driving signal transmitted from a driver Z82 according to a command from a CPU Z81.

The sampling nozzle Z5 has a shape whose distal end is tapered and whose vertical section along the axis is circle and on a side circumferential surface of which a sampling orifice Z51 is arranged.

Next, a procedure of conducting sampling of a small amount of the liquid sample S contained in the sample container Z3 by the use of the specimen sampling device Z1 in accordance with this embodiment will be explained with reference to FIG. 2 and FIG. 4.

First, as shown in FIG. 2, the sample container Z3, inner space of which the small amount of the liquid sample S is contained, is inserted into a hollow space of the compression coil spring Z2 so as to be fixed to the sample container case Z4. The internal space of the sample container case Z4 that accommodates the sample container Z3 is larger than the sample container Z3, and the sample container Z3 can be tilted in the specimen sampling device Z1. Next, the sample nozzle Z5 is moved by the position adjusting mechanism Z8 so as to be inserted into the sample container Z3 along an inner side surface (on the right as you face in FIG. 2) of the sample container Z3.

Figure 4:
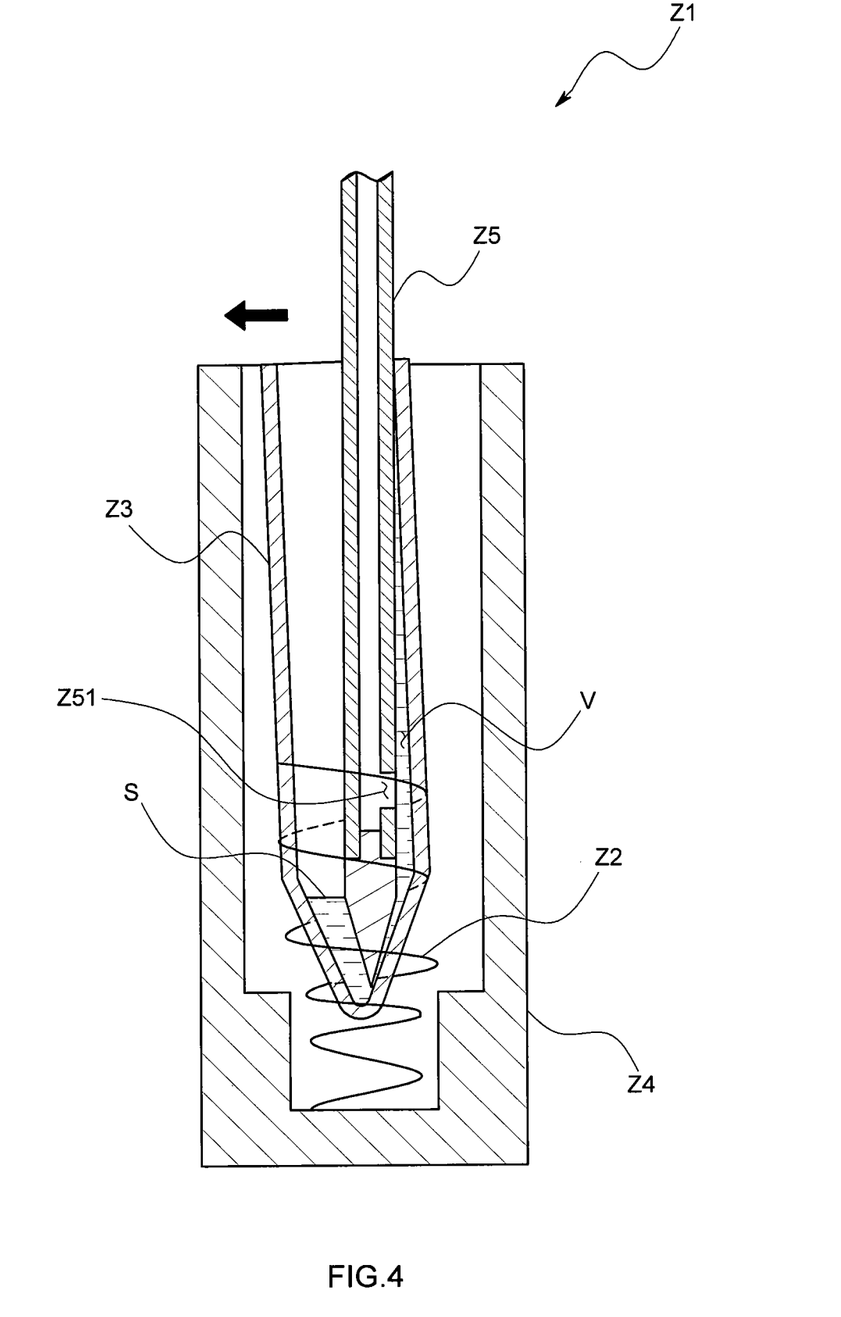
FIG. 4 is a pattern cross-sectional view of the specimen sampling device in accordance with this embodiment.

As shown in FIG. 2, in case of using the sample container Z3 having a shape of a bottom inner face that is tapered toward the bottom, if the sampling nozzle Z5 is gradually inserted into the sample container Z3 along the inner side surface of the sample container Z3, the sample container Z3 is gradually tilted toward the left side as you face in FIG. 4. Then a void V is formed between the inner surface of the sample container Z3 and the sampling nozzle Z5.

An angle between the axis of the sample container Z3 and the sampling nozzle Z5 is preferably less than or equal to 10°, and more preferably about 5°. The liquid sample S contained in the sample container Z3 moves upwards in the void V formed between the inner surface of the sample container Z3 and the sampling nozzle Z5 because of a capillary phenomenon and then reaches a position of the sampling orifice Z51 arranged on the side circumferential surface of the sampling nozzle Z5. As a result, it is possible to suck the liquid sample S even though the liquid sample S is in a small amount.

In accordance with the specimen sampling device Z1 in accordance with the second embodiment, when the sampling nozzle Z5 is inserted into inside of the sampling container Z3 along the inner side surface, since the sample container Z3 supported by the compression coil spring Z2 is tilted so that the void V is formed between the sample container Z3 and the sampling nozzle Z5 and the liquid sample S moves upwards in the void V due to the capillary phenomenon and then reaches the sampling orifice Z51, it is possible to suck the liquid sample S preferably even though an amount of the liquid sample S is small.

In addition, even though the distal end of the sampling nozzle Z5 touches the bottom of the'sample container Z3, a shock is absorbed by the compression coil spring Z2 because the sample container Z3 is supported by the compression coil spring Z2. Then a stress will not reach the sampling nozzle Z5, thereby causing no damage on an operating mechanism of the sampling nozzle Z5. As a result, it is possible to insert the sampling nozzle Z5 until the distal end of the sampling nozzle Z5 touches the bottom of the sampling container Z3, which enables sucking the liquid sample S preferably even though the liquid sample S is in a small amount.

<Third Embodiment>

Next, a third embodiment will be explained with reference to drawings. In the following explanation, the same components as those in the second embodiment are denoted by the same codes as those in the embodiment.

Figure 5:
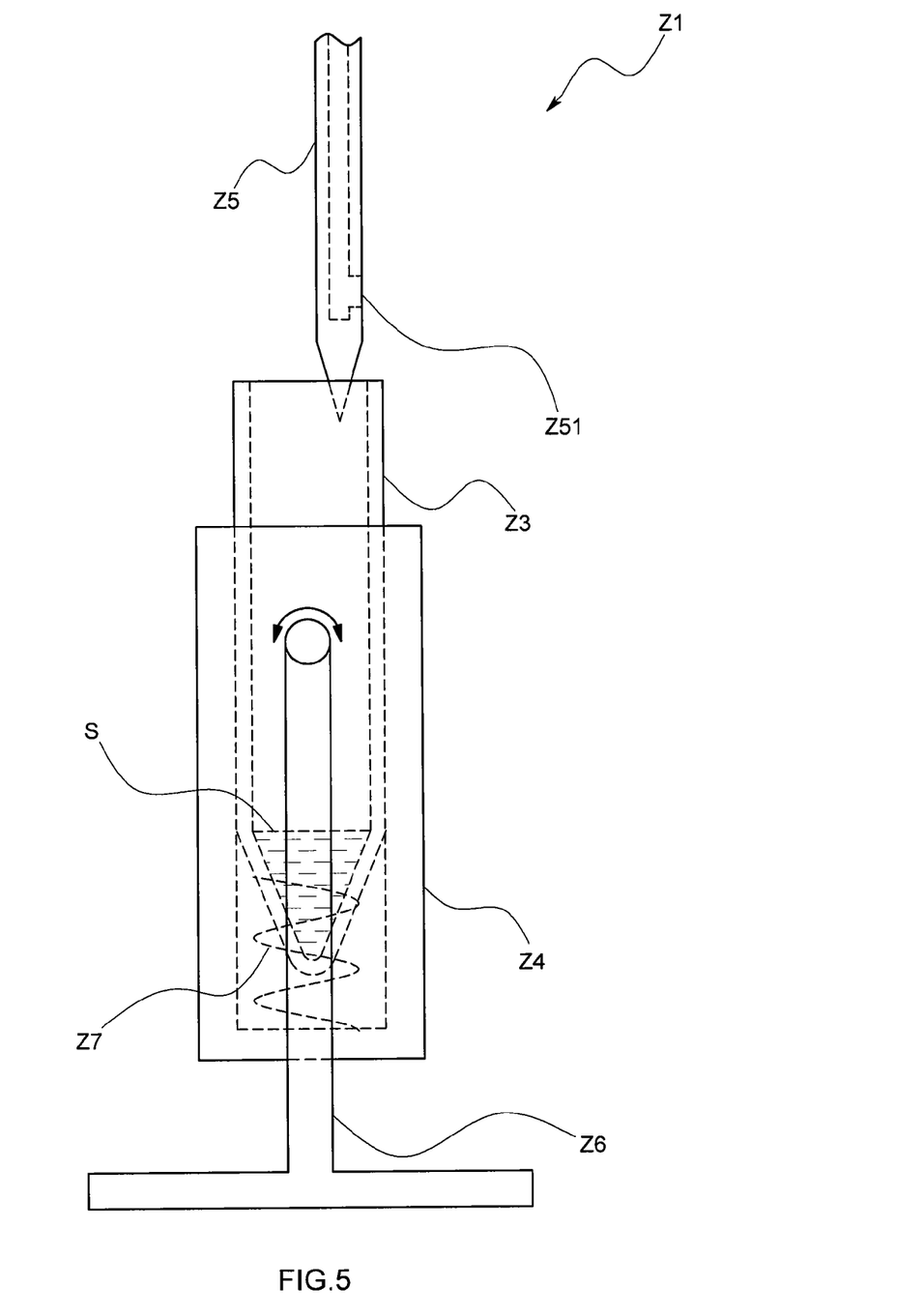
FIG. 5 is a pattern sectional side view of the specimen sampling device in accordance with another embodiment.
Figure 6:
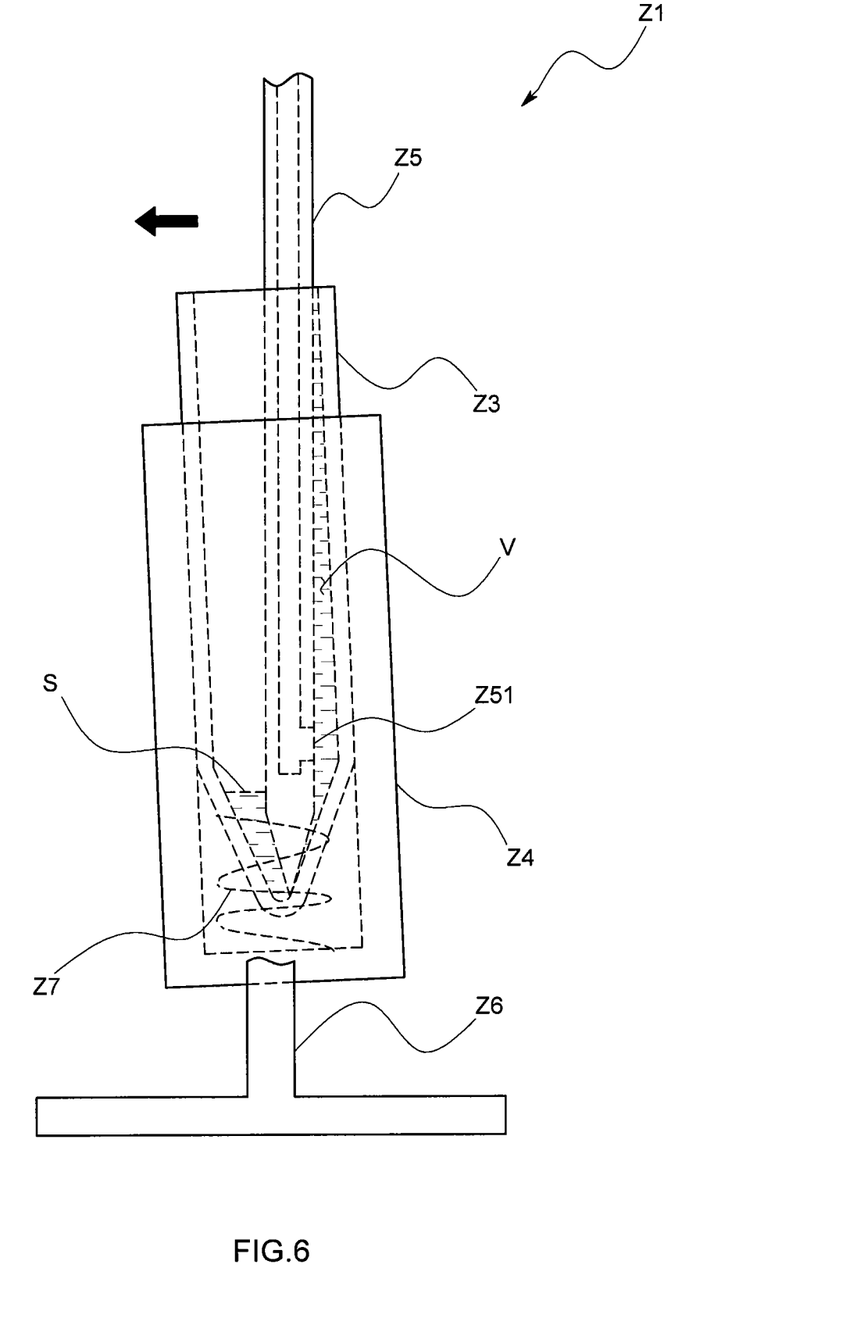
FIG. 6 is a pattern sectional side view of the specimen sampling device in accordance with this embodiment.

The specimen sampling device Z1 in accordance with the third embodiment comprises, as shown in FIG. 5 and FIG. 6, the sample container case Z4 as being an angle setting mechanism supported in a freely turnable manner by a stand Z6, a position adjusting mechanism Z8 and a sampling nozzle Z5.

The sample container case Z4 is supported in a freely turnable manner by the stand Z6, and a compression coil spring is arranged on its bottom as a buffer Z7. The sample container case Z4 has an internal space into which the sample container Z3 can fittingly insert.

Next, a procedure to conduct sampling of a small amount of the liquid sample S contained in the sample container Z3 by the use of the specimen sampling device Z1 in accordance with this embodiment will be explained with reference to FIG. 5 and FIG. 6.

First, as shown in FIG. 5, the sample container Z3, an internal space of which the small amount of the liquid sample S is contained, is inserted into the sample container case Z4 and fixed thereto. Next, the sampling nozzle Z5 is moved by the position adjusting mechanism Z8 so as to be inserted into the sample container Z3 along the inner side surface (on the right as you face in FIG. 5) of the sample container Z3.

As shown in FIG. 5, in case of using the sample container Z3 having a shape of a bottom inner face that is tapered toward the bottom, if the sampling nozzle Z5 is gradually inserted into the sample container Z3 along the inner side surface of the sample container Z3, the sample container case Z4 accommodating the sample container Z3 is gradually tilted toward the left side as you face in FIG. 6. Then a void V is formed between the inner surface of the sample container Z3 and the sampling nozzle Z5.

Even though a distal end of the sampling nozzle Z5 touches the bottom of the sample container Z3, the compression coil spring Z7 is compressed and absorbs a force that the distal end of the sampling nozzle Z5 pushes the bottom part of the sample container Z3.

The liquid sample S contained in the sample container Z3 moves upwards in the void V formed between the inner surface of the sample container Z3 and the sampling nozzle Z5 because of the capillary phenomenon and then reaches a position of the sampling orifice Z51 arranged on the side circumferential surface of the sampling nozzle Z5. As a result, it is possible to suck the liquid sample S preferably even though the liquid sample S is in a small amount.

With the specimen sampling device Z1 in accordance with the third embodiment, when the sampling nozzle Z5 is inserted into inside of the sampling container Z3 along the inner side surface, since the sample container Z3 supported by the freely turnable sample container case Z4 is tilted so that the void V is formed between the sample container Z3 and the sampling nozzle Z5 and the liquid sample S moves upwards in the void V due to the capillary phenomenon and then reaches the sampling orifice Z51, it is possible to suck the liquid sample S preferably even though the liquid sample S is in a small amount.

In addition, even though the distal end of the sampling nozzle Z5 touches the bottom of the sample container Z3, since a shock is absorbed by the compression coil spring Z7 because the compression coil spring Z7 is arranged on the bottom of the sample container case Z4, a stress will not reach the sampling nozzle Z5, thereby causing no damage on an operating mechanism of the sampling nozzle Z5. As a result, it is possible to insert the sampling nozzle Z5 until the distal end of the sampling nozzle Z5 touches the bottom of the sampling container Z3, which enables sucking the liquid sample S preferably even though the liquid sample S is in a small amount.

The present claimed invention is not limited to the above-mentioned second and third embodiments.

The position adjusting mechanism Z8 is not limited to the arrangement wherein the sampling nozzle Z5 is moved, and may be the arrangement that the position adjusting mechanism Z8 is provided for the sample container case Z4 or the stand Z6 and the sample container Z3 can be moved both horizontally and vertically relative to the fixed sampling nozzle A5. The angle setting mechanism is not limited to a mechanism wherein the sample container Z3 is supported in a freely turnable manner by the compression coil spring Z2 or the stand Z6, and may be a mechanism comprising multiple mutually exchangeable sample container cases Z4 wherein a tilt angle of a surface on which the sample container Z3 is placed is previously set for each type of the sample container Z3.

A shape of the sampling nozzle Z5 is not limited to a circle in a vertical section along its axis or a distal end of the sampling nozzle Z5 is tapered, and may be any shape as long as the sampling orifice Z51 opens at a lateral surface thereof.

In addition, a part or all of the above-mentioned embodiment or the modified embodiment may be appropriately combined, and it is a matter of course that the present claimed invention is not limited to the above-mentioned embodiment and may be variously modified without departing from a spirit of the invention.

Possible Applications in Industry

In accordance with this invention, it is possible to conduct accurate quantitative suction without being affected by a pressure at a time when the nozzle is inserted into the closed container.

The invention claimed is:

1. A nozzle device comprising:
a nozzle that is configured to be inserted into a closed container to remove a liquid stored in the closed container;
an exposure to atmosphere mechanism that is configured to enable the closed container to communicate directly with atmospheric air,
an opening/closing structure that is connected to an end part of the nozzle, the opening/closing structure having an internal flow channel communicated with a flow channel in the nozzle and an opening/closing mechanism for opening and closing the internal flow channel, and
an opening/closing control section that controls the opening/closing mechanism, wherein
the opening/closing structure includes a manifold having the internal flow channel in communication with the flow channel in the nozzle and a solenoid valve arranged in the manifold, and the opening/closing control section controls the solenoid valve to enable an accurate removal of the liquid by the nozzle, wherein
the opening/closing control section controls the opening/closing mechanism so as to block up the internal flow channel at a time when the nozzle is inserted into the closed container, wherein
the exposure to atmosphere mechanism comprises an opening part that is formed on the manifold and is configured to enable the closed container to communicate with ambient atmospheric air immediately adjacent to and surrounding the manifold.

2. The nozzle device described in claim 1, wherein the internal flow channel of the opening/closing structure is not transformed by a differential pressure between an atmospheric pressure and a pressure in the closed container.

3. The nozzle device described in claim 1, wherein the opening/closing control section controls the opening/closing mechanism so as to block up the internal flow channel until a predetermined time period after the nozzle is inserted into the closed container.

4. The nozzle device described in claim 1, wherein the opening/closing control section controls the opening/closing mechanism so as to block up the internal flow channel at a time when the nozzle is pulled out of the closed container.

5. The nozzle device described in claim 1, wherein the manifold is formed from a rigid material selected from one of aluminum, stainless steel, polyphenylsulphate resin and acrylic resin.

6. A liquid sample analyzer comprising:
the nozzle device described in claim 1, a suction mechanism that is connected to the opening/closing structure and that is to suck the liquid in the closed container through the nozzle, and a suction control section that controls the suction mechanism.

7. The liquid sample analyzer described in claim 6, wherein the suction control section sucks the liquid from the closed container at a time when a predetermined period passes after the nozzle is inserted into the closed container.

8. A nozzle device comprising:
a nozzle that is configured to be inserted into a closed container to remove a liquid stored in the closed container;
an exposure to atmosphere mechanism that is configured to enable the closed container to communicate directly with atmospheric air,
an opening/closing structure that is connected to an end part of the nozzle, the opening/closing structure having an internal flow channel communicated with a flow channel in the nozzle and an opening/closing mechanism for opening and closing the internal flow channel,
an opening/closing control section that controls the opening/closing mechanism, wherein the opening/closing structure includes a manifold having the internal flow channel in communication with the flow channel in the nozzle and a solenoid valve arranged in the manifold, and the opening/closing control section controls the solenoid valve to enable an accurate removal of the liquid by the nozzle, wherein the exposure to atmospheric mechanism is formed on the manifold and is configured to enable the closed container to communicate with ambient atmospheric air immediately adjacent to and surrounding the manifold, and
an information processing unit configured by a stored program to (1) insert the nozzle into the closed container after the opening/closing mechanism initially closes the flow channel and maintains a closed condition for a predetermined time period while the exposure to atmosphere mechanism is activated to enable atmospheric pressure to stabilize the pressure in the closed container and (2) after the predetermined time period to control the solenoid valve and to activate a suction mechanism to remove fluid from the closed container, wherein the information processing unit is further configured to subsequently close the internal flow channel and maintain the internal flow channel in a closed position during removal of the nozzle from the closed container.

9. A nozzle device consisting of:
a nozzle that is configured to be inserted into a closed container to remove a liquid stored in the closed container;
an exposure to atmosphere mechanism that is configured to enable the closed container to communicate directly with atmospheric air,
an opening/closing structure that is connected to an end part of the nozzle, the opening/closing structure having an internal flow channel communicated with a flow channel in the nozzle and an opening/closing mechanism for opening and closing the internal flow channel,
an opening/closing control section that controls the opening/closing mechanism, wherein the opening/closing structure includes a manifold having the internal flow channel in communication with the flow channel in the nozzle and a solenoid valve arranged in the manifold, and the opening/closing control section controls the solenoid valve to enable an accurate removal of the liquid by the nozzle, wherein the exposure to atmospheric mechanism is formed on the manifold and is configured to enable the closed container to communicate with ambient atmospheric air immediately adjacent to and surrounding the manifold, and an information processing unit configured by a stored program to (1) insert the nozzle into the closed container after the opening/closing mechanism initially closes the flow channel and maintains a closed condition for a predetermined time period while the exposure to atmosphere mechanism is activated to enable atmospheric pressure to stabilize the pressure in the closed container and (2) after the predetermined time period to control the solenoid valve and to activate a suction mechanism to remove fluid from the closed container, wherein the information processing unit is further configured to subsequently close the internal flow channel and maintain the internal flow channel in a closed position during removal of the nozzle from the closed container.

* * * * *